(12) United States Patent
Allen et al.

(10) Patent No.: US 9,827,074 B2
(45) Date of Patent: Nov. 28, 2017

(54) FIXED HYBRID DENTAL ATTACHMENT DEVICE AND METHODS OF USE

(71) Applicant: ZEST IP HOLDINGS, LLC, Escondido, CA (US)

(72) Inventors: Richard Robert Allen, Oceanside, CA (US); Christopher Michael Gervais, San Marcos, CA (US)

(73) Assignee: ZEST IP HOLDINGS, LLC, Carlsbad, CA (US)

( * ) Notice: Subject to any disclaimer, the term of this patent is extended or adjusted under 35 U.S.C. 154(b) by 0 days.

(21) Appl. No.: 14/806,616

(22) Filed: Jul. 22, 2015

(65) Prior Publication Data

US 2016/0022387 A1   Jan. 28, 2016

Related U.S. Application Data

(60) Provisional application No. 62/028,314, filed on Jul. 23, 2014, provisional application No. 62/027,780, filed on Jul. 22, 2014.

(51) Int. Cl.
*A61C 8/00* (2006.01)
*A61C 3/16* (2006.01)

(52) U.S. Cl.
CPC ............ *A61C 8/0053* (2013.01); *A61C 3/168* (2013.01); *A61C 8/006* (2013.01); *A61C 8/0062* (2013.01); *A61C 8/0068* (2013.01)

(58) Field of Classification Search
CPC ..... A61C 8/006; A61C 8/0062; A61C 8/0068; A61C 8/0053; A61C 5/08

(Continued)

(56) References Cited

U.S. PATENT DOCUMENTS

| 711,324 A | 10/1902 | Lacy |
| 3,514,858 A | 6/1970 | Silverman |

(Continued)

FOREIGN PATENT DOCUMENTS

| CH | WO 2014082744 A1 * | 6/2014 | ........... A61C 8/0048 |
| EP | 501940 A1 | 9/1992 | |

(Continued)

OTHER PUBLICATIONS

Langer, et al., "Tooth-Supported Telescopic Prostheses in Comprised Definitions: A clinical report" The Journal of Prosthetic Dentistry, 84 (2); 129-132 (2000).

(Continued)

*Primary Examiner* — Nicholas Lucchesi
*Assistant Examiner* — Shannel Wright
(74) *Attorney, Agent, or Firm* — Procopio, Cory, Hargreaves & Savitch, LLP

(57) ABSTRACT

A frictionally-retained detachable dental anchor device is provided for adjustably attaching a dental appliance with a tooth root or implant. The dental anchor device includes a cap secured in the dental appliance, an abutment attached with a tooth root or implant, and a compressible retention member with a first end in fixed attachment with the cap and a second end in snap engagement with the abutment via a frictionally-retained ball secured within a cavity of the abutment. The retention member is formed using a compressible material to allow the ball to compress and the retention member to flex while inserting the ball into the cavity. Additional friction-retained and fixed attachment configurations of the dental anchor device are provided, along with methods of securing a dental appliance in a subject's mouth by means of the friction-retained and fixed attachment dental anchor devices.

5 Claims, 21 Drawing Sheets

(58) Field of Classification Search
USPC .................................................. 433/171–173
See application file for complete search history.

(56) References Cited

U.S. PATENT DOCUMENTS

| | | | |
|---|---|---|---|
| 3,732,621 A * | 5/1973 | Bostrom | A61C 8/0022 433/174 |
| 3,787,975 A | 1/1974 | Zuest | |
| 3,990,150 A | 11/1976 | Giovannini | |
| 3,991,472 A * | 11/1976 | Lukesch | A61C 13/2656 433/169 |
| 4,158,256 A | 6/1979 | Wiland et al. | |
| 4,290,755 A | 9/1981 | Scott | |
| 4,362,509 A | 12/1982 | Sulc | |
| 4,431,416 A | 2/1984 | Niznick et al. | |
| 4,475,891 A | 10/1984 | Hader | |
| 4,488,874 A | 12/1984 | Soifer et al. | |
| 4,488,875 A | 12/1984 | Niznick et al. | |
| 4,518,357 A | 5/1985 | Brinkmann et al. | |
| 4,540,367 A | 9/1985 | Sulc | |
| 4,547,156 A | 10/1985 | Hader | |
| 4,568,285 A * | 2/1986 | Chiaramonte | A61C 8/0018 433/169 |
| 4,626,213 A | 12/1986 | Shiner et al. | |
| 4,645,453 A * | 2/1987 | Niznick | A61C 8/0018 433/173 |
| 4,657,510 A | 4/1987 | Gittleman et al. | |
| 4,738,623 A | 4/1988 | Driskell et al. | |
| 4,780,080 A | 10/1988 | Haris et al. | |
| 4,793,808 A | 12/1988 | Kirsch | |
| 4,832,601 A | 5/1989 | Linden et al. | |
| 4,854,872 B1 | 8/1989 | Detsch | |
| 4,907,969 A * | 3/1990 | Ward | A61C 8/005 433/173 |
| 4,932,868 A * | 6/1990 | Linkow | A61C 8/0018 433/174 |
| 4,934,935 A | 6/1990 | Edwards et al. | |
| 4,957,438 A | 9/1990 | Bax | |
| 4,988,297 A | 1/1991 | Lazzara et al. | |
| 5,030,095 A | 7/1991 | Niznick et al. | |
| 5,049,072 A * | 9/1991 | Lueschen | A61C 13/2656 433/173 |
| 5,071,350 A * | 12/1991 | Niznick | A61C 8/005 433/173 |
| 5,073,110 A | 12/1991 | Barbone | |
| 5,092,770 A | 3/1992 | Zakula | |
| 5,120,222 A | 6/1992 | Sulc | |
| 5,133,662 A * | 7/1992 | Metcalfe | A61C 8/0031 433/169 |
| 5,145,372 A | 9/1992 | Daftary et al. | |
| 5,178,539 A * | 1/1993 | Peltier | A61C 8/005 433/173 |
| 5,194,000 A | 3/1993 | Dury | |
| 5,195,891 A | 3/1993 | Sulc et al. | |
| 5,211,561 A | 5/1993 | Graub | |
| 5,302,125 A * | 4/1994 | Kownacki | A61C 8/0048 433/172 |
| 5,413,480 A | 5/1995 | Musikant et al. | |
| 5,417,570 A * | 5/1995 | Zuest | A61C 13/2656 433/172 |
| 5,480,304 A | 1/1996 | Nardi et al. | |
| 5,520,540 A | 5/1996 | Nardi et al. | |
| 5,527,182 A | 6/1996 | Willoughby | |
| 5,556,280 A | 9/1996 | Pelak | |
| 5,564,924 A | 10/1996 | Kwan et al. | |
| 5,599,185 A * | 2/1997 | Greenberg | A61C 8/008 433/173 |
| 5,630,717 A * | 5/1997 | Zuest | A61C 8/0048 433/172 |
| 5,636,989 A | 6/1997 | Somborac et al. | |
| 5,639,239 A | 6/1997 | Earle | |
| 5,662,475 A * | 9/1997 | Mena | A61C 8/005 433/172 |
| 5,678,997 A | 10/1997 | De Buck | |
| 5,839,898 A | 11/1998 | Fernandes | |
| 5,888,218 A * | 3/1999 | Folsom | A61C 8/0018 433/172 |
| 5,890,902 A * | 4/1999 | Sapian | A61C 8/0048 433/173 |
| 5,954,505 A | 9/1999 | Ford | |
| 5,993,212 A | 11/1999 | Shiner | |
| 6,030,219 A * | 2/2000 | Zuest | A61C 8/0048 433/172 |
| 6,287,115 B1 * | 9/2001 | Lustig | A61C 8/0022 433/172 |
| 6,299,447 B1 * | 10/2001 | Zuest | A61C 8/0048 433/172 |
| 6,302,693 B1 * | 10/2001 | Mena | A61C 8/0048 433/169 |
| 6,332,777 B1 | 12/2001 | Sutter | |
| 6,500,003 B2 * | 12/2002 | Nichinonni | A61C 8/005 433/173 |
| 6,716,030 B1 | 4/2004 | Bulard et al. | |
| 6,843,653 B2 * | 1/2005 | Carlton | A61C 8/005 433/174 |
| 6,981,871 B2 | 1/2006 | Mullaly et al. | |
| 7,214,063 B2 * | 5/2007 | Cohen | A61C 8/005 433/173 |
| 7,704,076 B2 * | 4/2010 | Mullaly | A61C 8/0018 433/172 |
| 7,959,439 B2 * | 6/2011 | Bulloch | A61C 8/0048 433/172 |
| 8,128,403 B2 | 3/2012 | Karmon | |
| D666,298 S | 8/2012 | Sibhatu et al. | |
| 8,684,733 B2 * | 4/2014 | Mcbride | A61C 8/0053 433/173 |
| 9,456,881 B1 * | 10/2016 | Niznick | A61C 8/0053 |
| 2002/0177103 A1 | 11/2002 | Pelak | |
| 2003/0224329 A1 * | 12/2003 | Carlton | A61C 8/005 433/173 |
| 2003/0224331 A1 | 12/2003 | Kumar et al. | |
| 2005/0019730 A1 | 1/2005 | Gittleman | |
| 2006/0024644 A1 * | 2/2006 | Cohen | A61C 8/005 433/173 |
| 2006/0275735 A1 | 12/2006 | Bulard et al. | |
| 2008/0153063 A1 * | 6/2008 | Mullaly | A61C 8/0018 433/174 |
| 2008/0241790 A1 * | 10/2008 | Gittleman | A61C 8/0053 433/174 |
| 2009/0155745 A1 | 6/2009 | Laux | |
| 2009/0202962 A1 * | 8/2009 | Xam-Mar Mangrane | A61C 8/005 433/173 |
| 2009/0246734 A1 | 10/2009 | Bar Shalom | |
| 2010/0055645 A1 | 3/2010 | Mullaly et al. | |
| 2010/0129773 A1 | 5/2010 | Chen | |
| 2010/0159420 A1 | 6/2010 | Mullaly et al. | |
| 2010/0232869 A1 | 9/2010 | Ditzler et al. | |
| 2010/0330536 A1 | 12/2010 | Mullaly | |
| 2012/0045737 A1 | 2/2012 | Ang | |
| 2012/0214128 A1 | 8/2012 | Collins et al. | |
| 2012/0288827 A1 * | 11/2012 | McBride | A61C 8/0053 433/174 |
| 2012/0295223 A1 | 11/2012 | Robb et al. | |
| 2012/0315599 A1 * | 12/2012 | Mullaly | A61C 8/0048 433/173 |
| 2013/0209957 A1 | 8/2013 | Sanchez et al. | |
| 2014/0162211 A1 * | 6/2014 | Mullaly | A61C 8/0053 433/172 |
| 2014/0162212 A1 * | 6/2014 | Mullaly | A61C 8/0053 433/173 |

FOREIGN PATENT DOCUMENTS

| | | | |
|---|---|---|---|
| ES | EP 2647347 A1 * | 10/2013 | A61C 8/0053 |
| IL | EP 1621156 A1 * | 2/2006 | A61C 8/005 |
| WO | WO 0028914 A2 * | 5/2000 | A61C 8/0022 |
| WO | 2008040134 A1 | 4/2008 | |

(56) References Cited

FOREIGN PATENT DOCUMENTS

| | | |
|---|---|---|
| WO | 2009156601 A2 | 12/2009 |
| WO | 2010048558 A2 | 4/2010 |

OTHER PUBLICATIONS

International Search Report and Written Opinion for PCT/US2015041634, dated Oct. 16, 2015, 5 pages.
International Search Report and Written Opinion for PCTUS2016060845, dated Feb. 16, 2017, 16 pages.

* cited by examiner

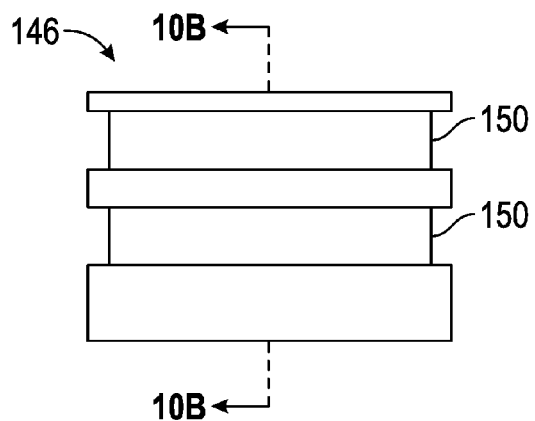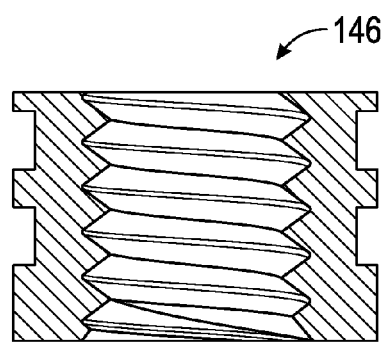
FIG. 10A
FIG. 10B
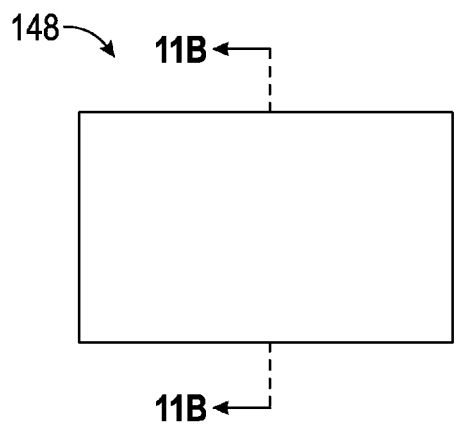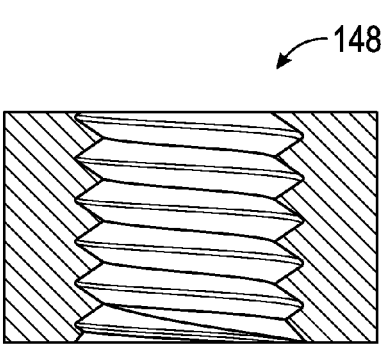
FIG. 11A
FIG. 11B

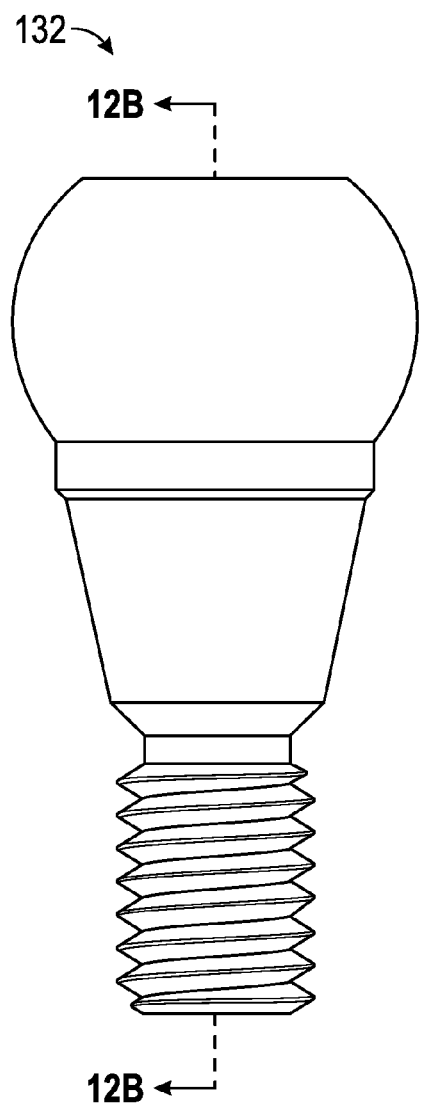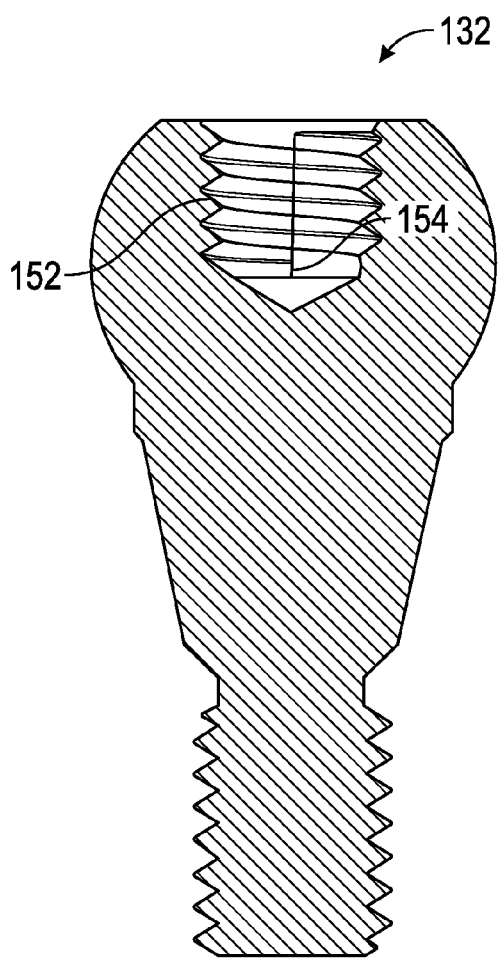
FIG. 12A
FIG. 12B

FIXED HYBRID DENTAL ATTACHMENT DEVICE AND METHODS OF USE

BACKGROUND

Field of the Invention

Devices and methods provided herein relate to a dental attachment assembly for anchoring a dental appliance with a base structure such as a tooth root or dental implant, and more specifically to a frictionally-retained compressible ball and socket assembly which adjustably attaches the dental appliance with the base structure.

Related Art

Dental anchoring assemblies are utilized to anchor a dental appliance with a dental implant or tooth root, typically by fitting two or more partially-movable components together to provide an improved fit and comfort. In some assemblies, male and female parts have mating, snap engageable formations for releasably securing the male part to the female part. For example, the female part has a socket and the male part has a head for snap engagement in the socket. However, as repeated impacts of the socket and head may damage the retentive head of the male and cause wearing due to friction of the components as they move, a compressible annular ring may be provided to absorb the frictional forces and act as a cushion between the socket and the head. However, even the ring may wear out over a period of time and need to be replaced, requiring regular maintenance of the dental anchoring assembly that is uncomfortable and inconvenient for the patient. Furthermore, to allow the compressible annular ring to be easily removed and replaced, the ring may be provided with a securing mechanism on a mating surface with the socket (such as a threaded portion), which further adds to the cost and complexity of the dental anchor assembly.

It is therefore desirable to avoid the need for continued maintenance and simplify the design of the dental anchoring assembly.

SUMMARY

Embodiments described herein provide for a frictionally-retained detachable dental anchor device for adjustably attaching a dental appliance with a tooth root or implant. The dental anchor device includes a cap secured in the dental appliance, an abutment attached with a tooth root or implant, and a compressible retention member with a first end in fixed attachment with the cap and a second end in snap engagement with the abutment via a frictionally-retained ball secured within a cavity of the abutment. The retention member is formed using a compressible material to allow the ball to compress and the retention member to flex while inserting the ball into the cavity. Additional friction-retained and fixed attachment configurations of the dental anchor device are provided, along with methods of securing a dental appliance in a subject's mouth by means of the friction-retained and fixed attachment dental anchor devices.

In one aspect of the invention, a dental attachment assembly comprises a cap for securing with a dental appliance, the cap having an open end defining an inner cavity; an abutment configured with an upper opening with a socket; and a retention member configured with a threaded portion to securely attach with the cap at a first end and configured with a spherical head to frictionally detachably attach with the socket of the abutment at a second end to form a frictional fit between the head and the socket and securely retain the dental appliance and abutment.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 10A is a side view of an acrylic pick up cap embodiment of the denture cap, according to an embodiment of the invention;

FIG. 10B is a side cutout view on the lines 10B-10B of FIG. 10A;

FIG. 11A is a side view of a burn out cap embodiment of the denture cap, according to an embodiment of the invention;

FIG. 11B is a side cutout view on the lines 11B-11B of FIG. 11A;

FIG. 12A is a side view of the abutment of the outer surface retention configuration, according to an embodiment of the invention;

FIG. 12B is a side cutout view on the lines 12B-12B of FIG. 12A;

DETAILED DESCRIPTION

Figure 1:
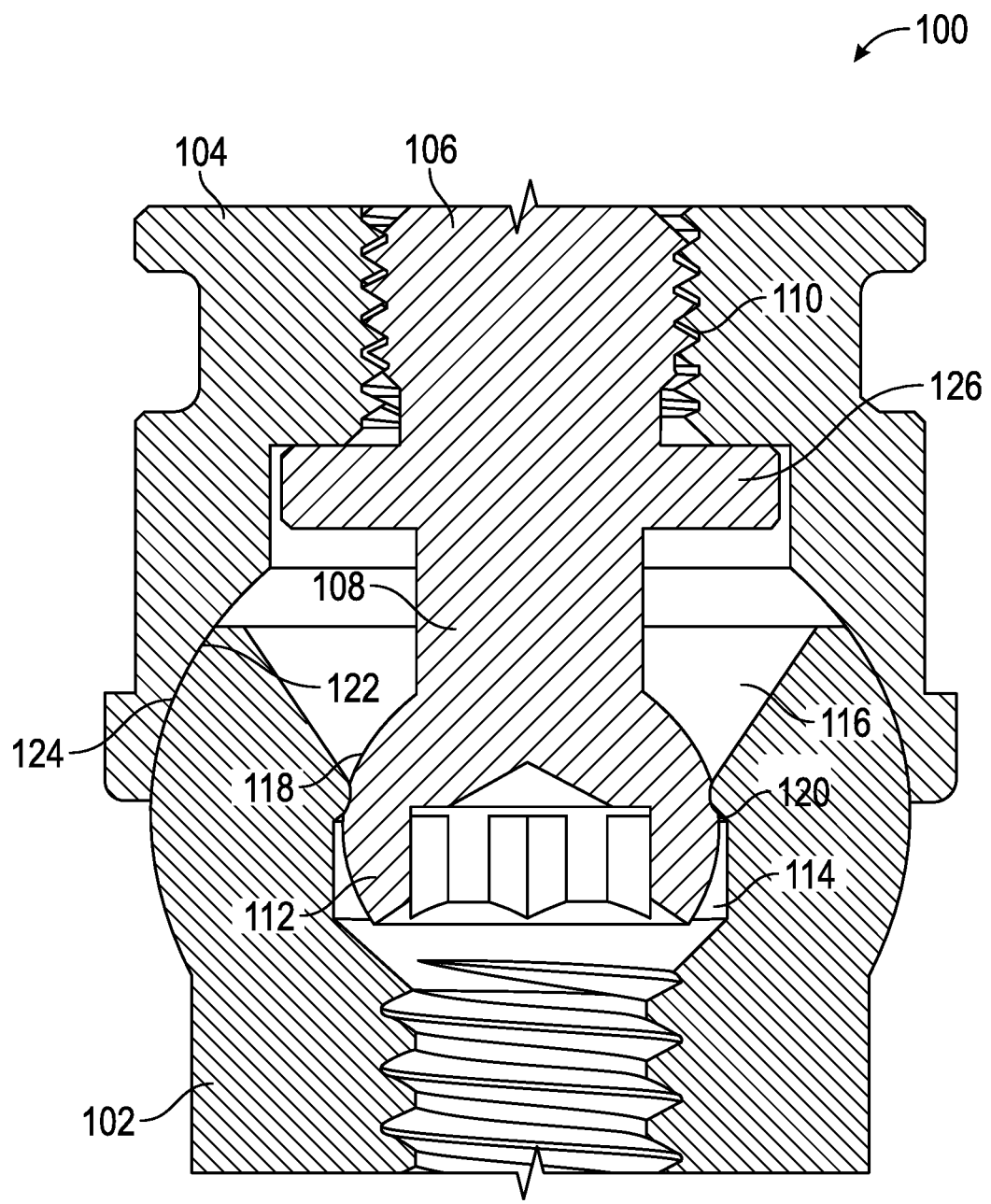
FIG. 1 is a side cutout view illustration of an abutment, retention member, and cap of a dental attachment assembly, according to an embodiment of the invention.

Certain embodiments disclosed herein provide for a frictionally-retained detachable dental anchor device or dental attachment assembly for adjustably attaching a dental appliance with a tooth root or implant. The dental anchor device includes a cap or denture attachment housing secured in the dental appliance, an abutment attached with a tooth root or implant, and a compressible retention member with a first end in fixed attachment with the cap and a second end in snap engagement with the abutment via a frictionally-retained ball secured within a cavity of the abutment. The retention member is formed using a compressible material to allow the ball to compress and the retention member to flex while inserting the ball into the cavity. Additional friction-retained and fixed attachment configurations of the dental anchor device are provided, along with methods of securing a dental appliance in a subject's mouth by means of the friction-retained and fixed attachment dental anchor devices.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

The dental attachment device described herein functions similar to a fixed dental attachment system, yet can be more easily removed by a dental professional using a special tool. The dental attachment device described herein is useful to attach a dental appliance, such as a denture, with an implant and provide a retentive force of about 10 to 75 pounds, while also providing ease of engagement of the retentive member with the abutment due to the compressible nature of the materials used and the friction-retained snap-fit of the ball and socket components.

As will be described in detail below, the retentive or retention member is formed from a compressible material— such as a polymer or soft metal—to allow the retention member to compress and flex while being attached or detached from an abutment secured to the implant. The compressible and flexible retention member can then be secured with the abutment at a variety of angles, which is often necessary when securing a dental appliance to a plurality of implants extending at different angles across a person's upper or lower jaw. Additionally, the compressible ball eliminates the need for a separate compressible annular ring to be positioned in the socket of the abutment between the retention member and interior abutment walls, as well as the need for a securing mechanism for securing the annular ring to the abutment walls. The dental anchoring device is therefore easier to manufacture and requires less maintenance once inserted.

A. Dental Attachment Assembly

FIG. 1 illustrates one embodiment of the dental anchoring device 100 which may be attached with an implant (not shown) that may be anchored to a bone or other base structure (not shown) such as a tooth root. The assembly includes an abutment 102 which is secured to the implant and a cap 104 which is secured in a recess of a dental appliance. A retention member 106 serves to provide the frictionally-retained connection between the cap and the abutment. To this end, the retention member includes a shaft 108 which is threaded at a first end 110 in a threaded connection with the cap. A second end of the shaft which interfaces with the abutment includes a head 112 which is substantially spherical in shape and which is configured to create a frictional fit with a socket 114 found in an upper opening 116 of the abutment. The head includes a curved surface 118 configured to frictionally fit with a corresponding recessed surface 120 of the socket. Specifically, in the area of the recessed surface is an undercut that is engaged with the head 112, but the socket does not necessarily need to be curved to match the curved surface 118 of the head 112. In the embodiment in FIG. 1, the side walls of the head 112 are convex, while the top of the head is flat in order to provide for a closer fit of the head 112 with the abutment. The inner surface of the opening 116 of the abutment narrows in diameter to a point where it is configured to securely fit the corresponding diameter of the head 112 at the mouth of the socket 114.

One benefit of the compressible material for the retentive member 106 is that the diameter of the head 112 may be altered to increase or decrease the retentive force provided by the frictional-fit of the head 112 and socket 114. The greater the diameter, the more retentive force will be provided, while a smaller diameter head 112 will provide less retentive force. As mentioned above, the retentive force may vary from anywhere between about 10 to about 75 pounds, although some embodiments may provide as little as about 1 pound of retentive force for use in the initial positioning of the dental appliance and dental anchoring device.

Figure 1B:
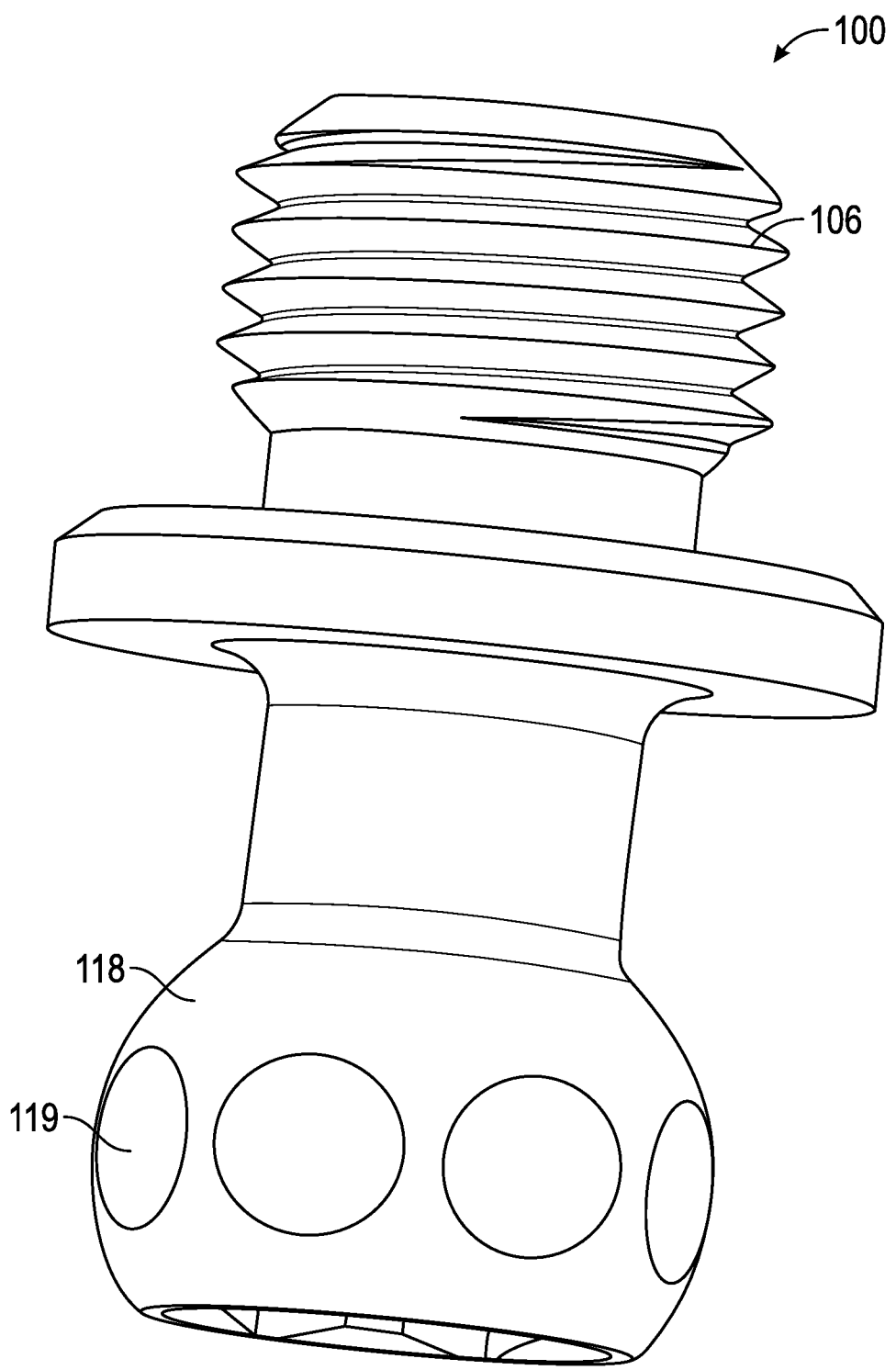
FIGS. 1B and 1C illustrate side views of flat surfaced retention heads, according to one embodiment of the invention.
Figure 1C:
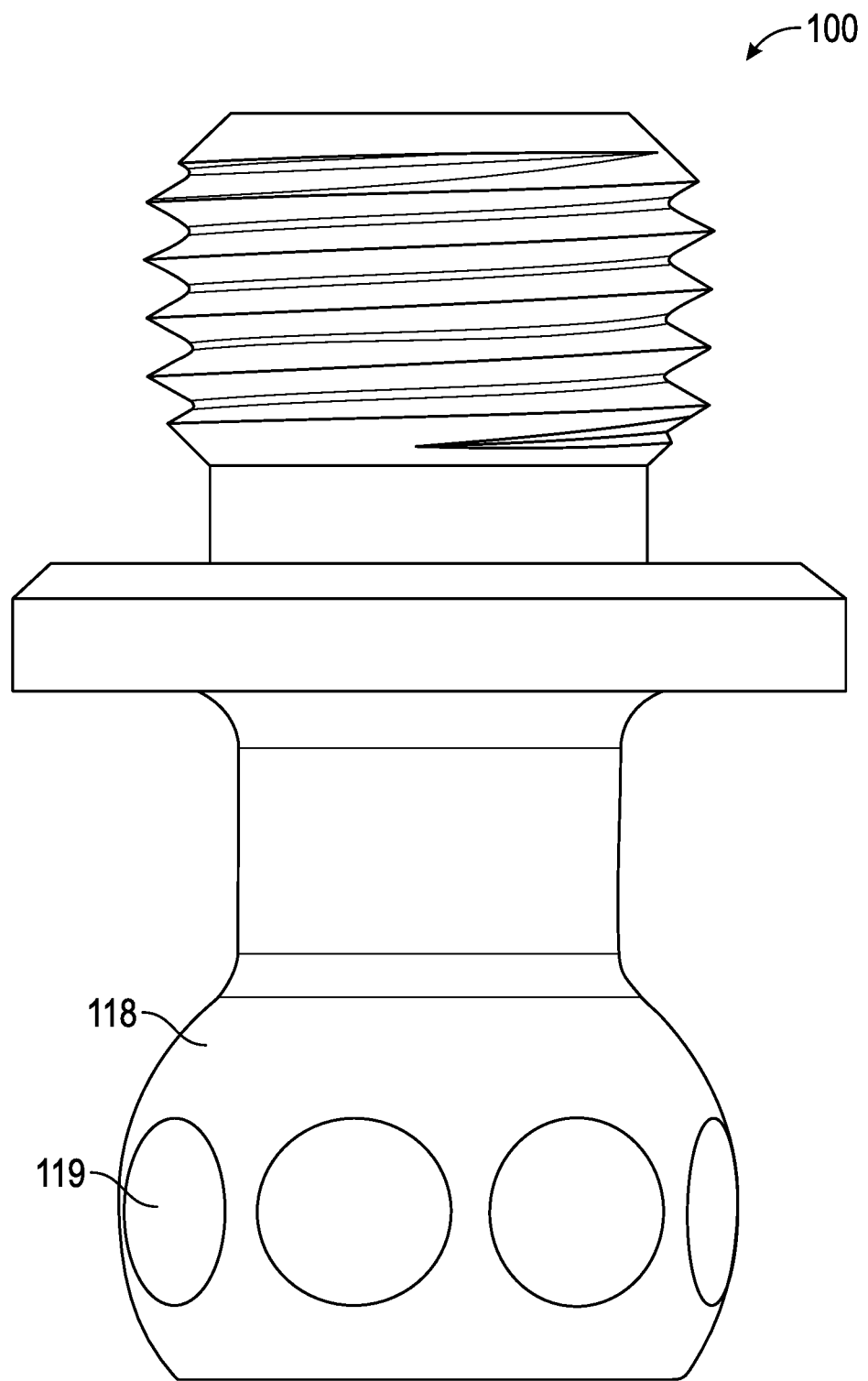

In another embodiment illustrated in FIG. 1B and FIG. 1C, one or more sides of the curved surface 118 may have flattened portions 119 to reduce the amount of friction between the curved surface 118 of the head and the corresponding curved surface 120 of the socket.

The cap 104 is configured with an annular surface 122 which may be curved to engage with a corresponding curved outer surface 124 of the abutment, providing an additional frictional fit for the dental attachment assembly.

In one embodiment, a ball flange 126 may be provided as one or more protrusions extending perpendicular to the axial direction of the shaft 108 and which are configured to contact the cap 104. The ball flange 126 serves to help locate the ball 112 within the socket 114 and cap 104 and prevent vertical movement of the assembly.

In the embodiment described herein, the retention member may be formed from a compressible or elastomeric material such as a polymer or a soft metal, non-limiting examples of which include polyether ether ketone (PEEK), nickel titanium (nitinol), pink TiCN coating or titanium. In one embodiment, the surfaces may be coated with a gold nitride coating to reduce friction.

Figure 2:
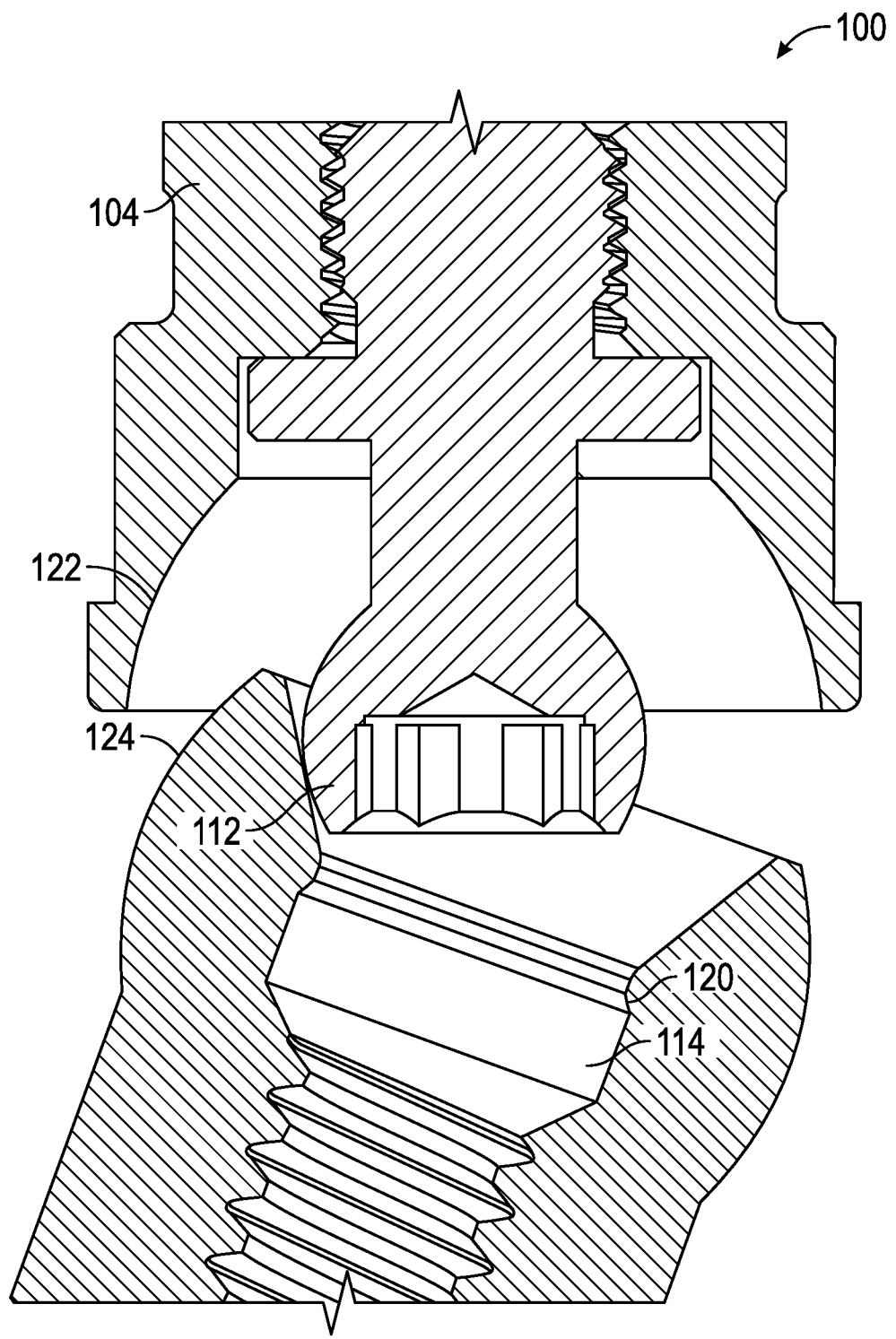
FIG. 2 is a side cutout view illustration of the dental attachment assembly in an angled, unattached configuration, according to one embodiment of the invention.

FIG. 2 is a side cutout view illustration of the dental anchoring device in an angled, unattached configuration illustrating the varying angles at which the retentive member 106 may be snap-fit into the abutment. In practical applications, the implant may protrude from the bone or tooth root at varying angles from the ideal vertical angle due to the structure of the bone or the placement of the implant during surgery. The dental anchoring device therefore corrects any angular displacement due to the rotation of the head 112 in the socket 114. In one embodiment, the angle of approach of the retentive head with respect to the abutment may vary up to about 20 degrees in any direction from the vertically-aligned orientation shown in FIG. 1. In combination with another implant also offset at a similar angle, the dental anchoring device may therefore provide as much as about 40 degrees of angle correction.

Figure 3:
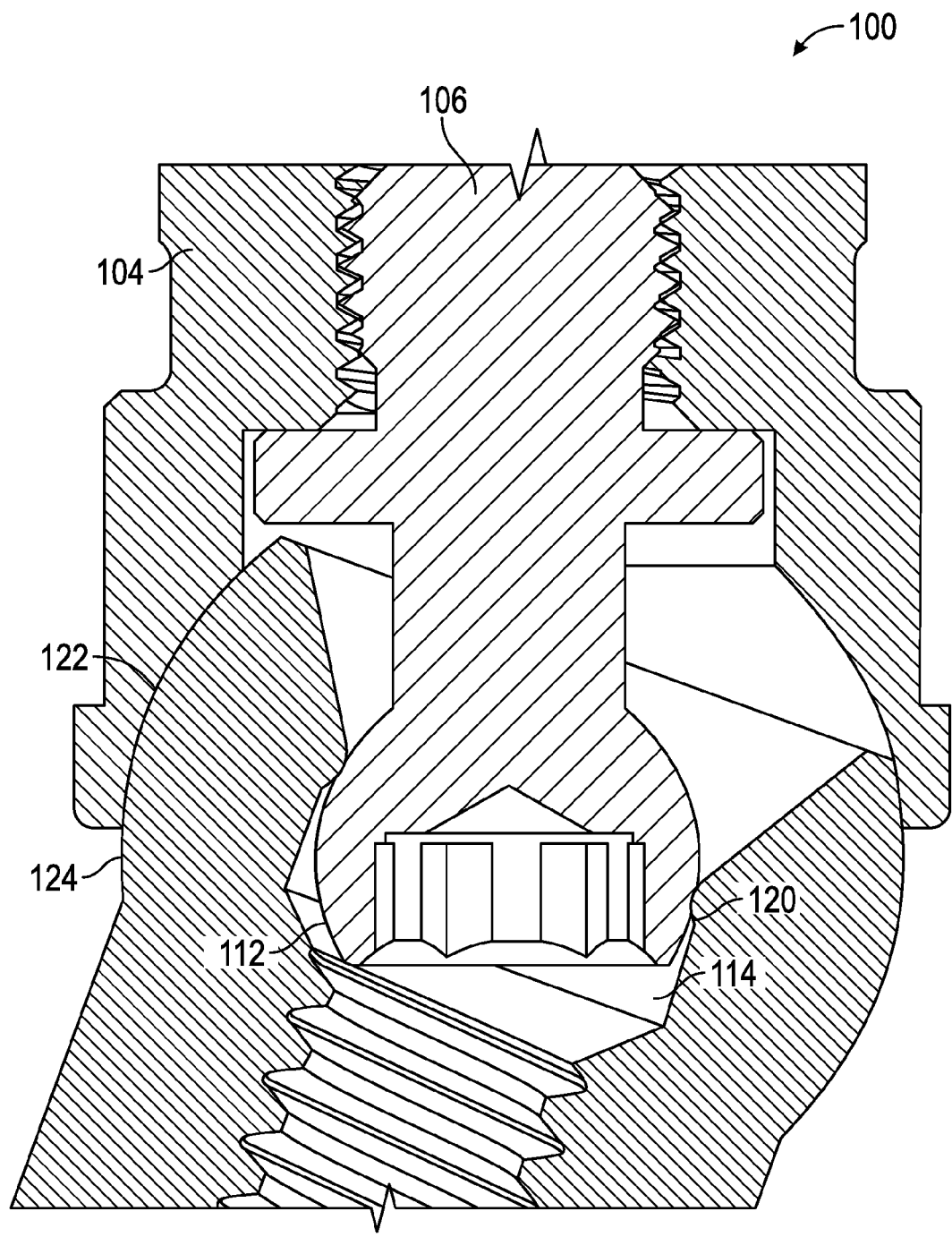
FIG. 3 is a side cutout view illustration of the dental attachment assembly in an attached, angled configuration, according to one embodiment of the invention.

FIG. 3 is a side cutout view illustration of the dental attachment assembly in the angled orientation shown in FIG. 2 but where the retentive member 106 is now snap-fit into the socket 114 of the abutment 102. As illustrated in FIG. 3, the head 112 may be secured within the socket 114 despite the differential angle. Furthermore, the annular surface 122 of the cap 104 is also still fitted around the outer curved surface 124 of the abutment.

Figure 4A:
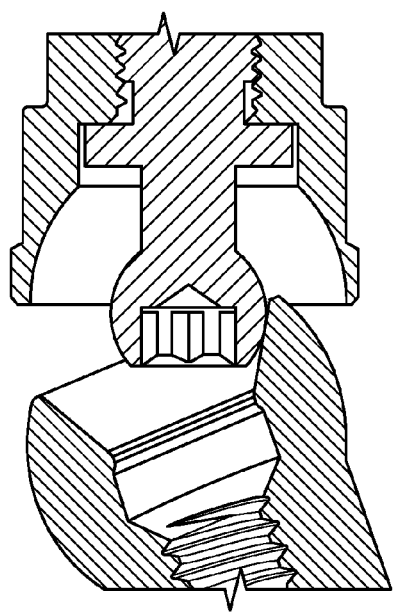
FIGS. 4A, 4B and 4C are side cutout view illustrations of a process of attaching the retention member with the abutment illustrating a compression of a ball and shaft portion of the retention member, according to an embodiment of the invention.
Figure 4C:
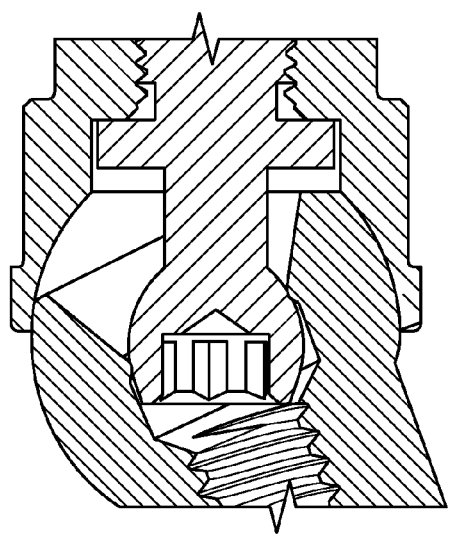
Figure 4B:
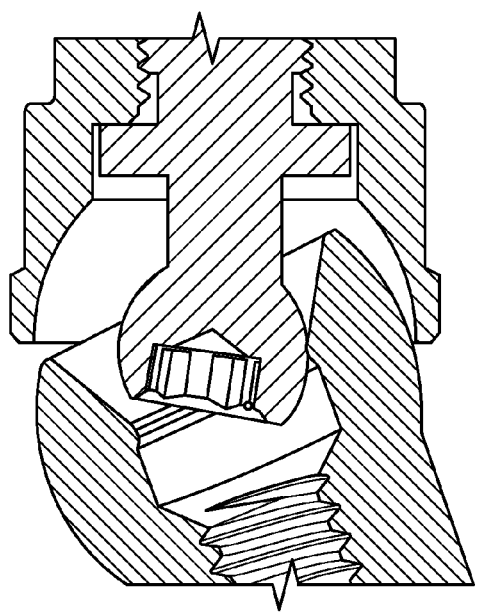

FIGS. 4A-4C are side cutout view illustrations of the flexing and compression of the head 112 and shaft 108 of the retention member 106 during a process of attaching the retention member with the abutment at the angle already illustrated in FIGS. 2 and 3, according to an embodiment of the invention. As illustrated specifically in FIG. 4B, the shaft 108 and head 112 of the retention member 106 are flexing and compressed due to the angle of the abutment with respect to the retention member 106. However, as shown in FIG. 4C, once the retention member 106 is frictionally snap-fit into the socket 114, the flexure and compression has been reduced such that the retention member 106 and abutment 102 provide a secure fit without inducing an undue amount of stress on the retentive member.

B. Screw-Retained Configuration

Figure 5:
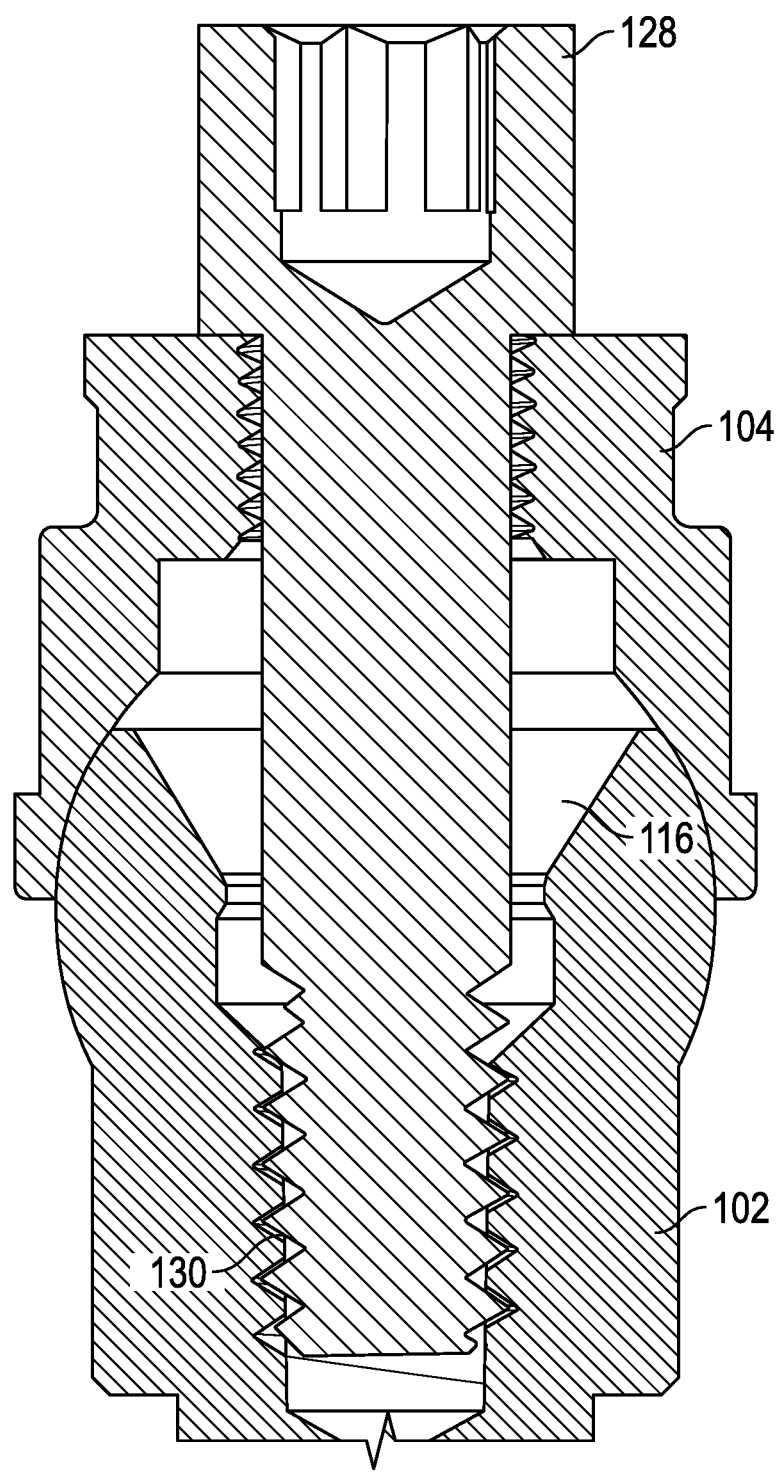
FIG. 5 is a side cutout view illustration of a screw-retained dental attachment assembly, according to an embodiment of the invention.

FIG. 5 is a side cutout view illustration of a screw-retained dental attachment assembly, according to an embodiment of the invention, where instead of the ball and socket configuration, a cantilevered screw 128 protrudes through the cavity 116 in the abutment 102 and forms a threaded connection 130 with the abutment 102 to create a fixed connection. As illustrated above with regard to FIG. 1, the annular surface 122 of the cap 104 provides a sliding retentive surface with the outer curved surface 124 of the abutment to allow for minimal rotation of the screw 128 and cap 104 with respect to the abutment.

This embodiment is useful for obtaining a highly secure fit between an implant and the dental appliance which will provide a significant retentive force. As described further below, this configuration may only be needed for one implant where several implants are being used to secure a dental appliance across the surface of a person's mouth.

C. Outer Surface Retention Configuration

Figures 6A, 6B:
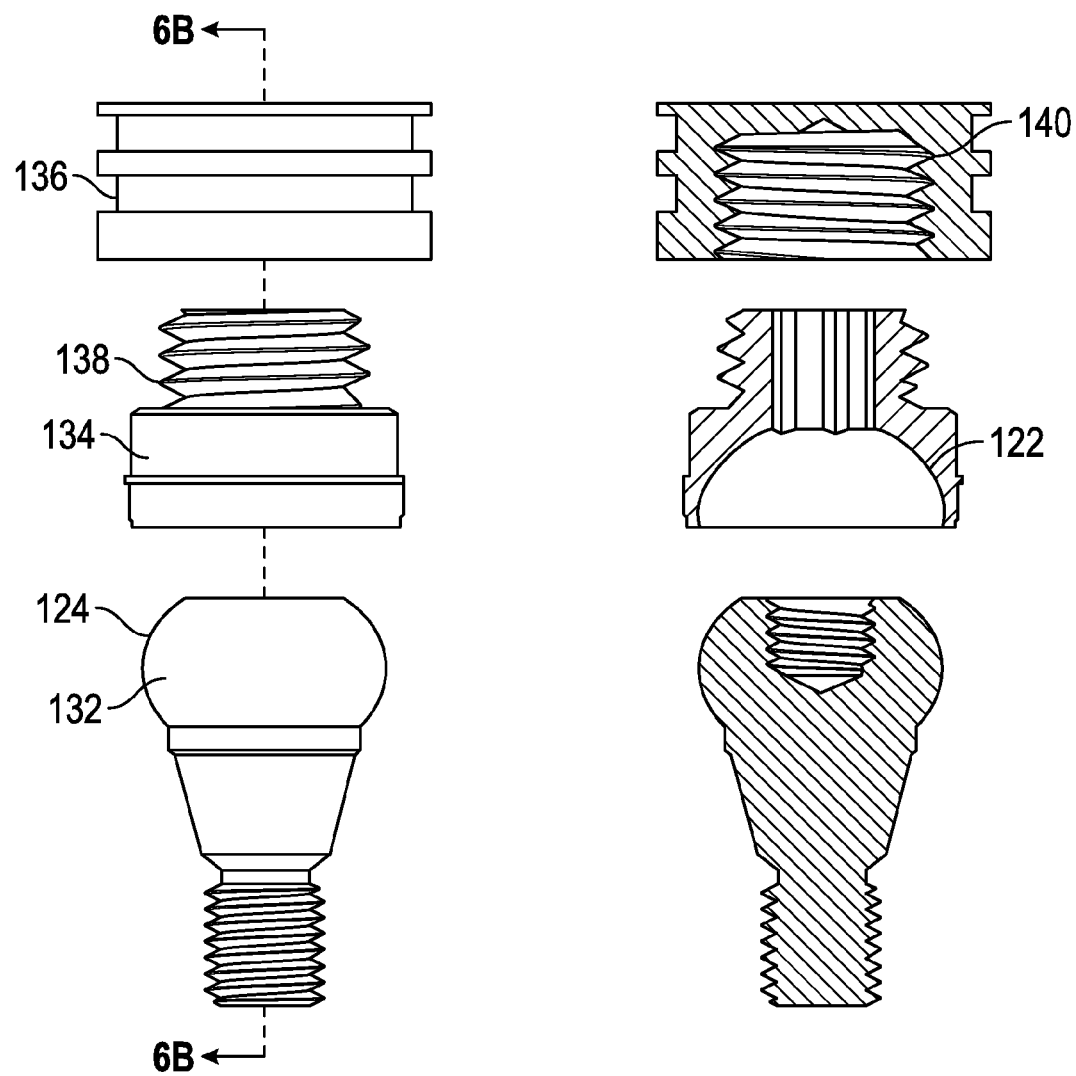
FIG. 6A is an exploded view of a denture cap or attachment housing, retention member and abutment of an outer surface retention configuration of a dental attachment assembly, according to an embodiment of the invention.
FIG. 6B is an exploded cross-sectional view on the lines 6B-6B of FIG. 6A.
Figure 7A:
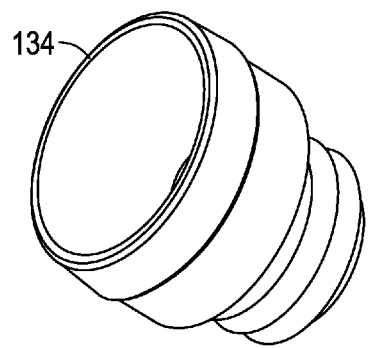
FIG. 7A is a bottom side perspective view illustration of the retention cap of the outer surface retention configuration, according to one embodiment of the invention.
Figure 7B:
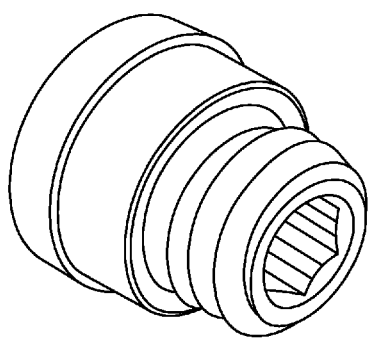
FIG. 7B is a top side perspective view illustration of the retention cap of the outer surface retention configuration, according to one embodiment of the invention
Figure 7C:
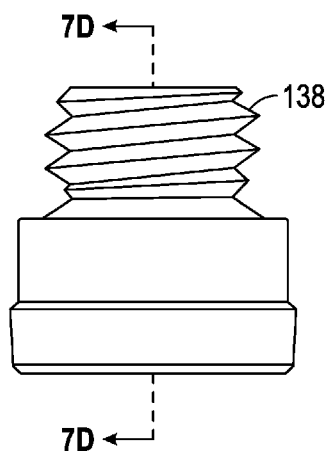
FIG. 7C is a side view illustration of the retention cap of the outer surface retention configuration, according to one embodiment of the invention
Figure 7D:
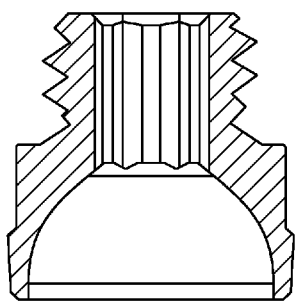
FIG. 7D is a side cutout view illustration of the retention member of the outer surface retention configuration along lines 7D-7D of FIG. 7C, according to an embodiment of the invention.

In another alternative embodiment, an abutment 132 may be utilized with a retentive cap 134 and a denture cap 136 to provide retentive force on the outer surface of the abutment without the use of the head and socket configuration. FIGS. 6A and 6B are exploded view illustrations of the denture cap 136, retention cap 134 and abutment 132 of an outer surface retention configuration of a dental attachment assembly, according to an embodiment of the invention. As illustrated herein and also above in FIG. 1, the outer surface 124 of the abutment 130 forms a curved surface which mates with a corresponding curved surface 122 of the retention cap 132 to form a frictional fit. The retentive cap 134 may then be threaded with the denture cap 136 using a threaded surface 138 on the retentive cap 134 and a corresponding threaded surface 140 on the denture cap 136.

Figure 8:
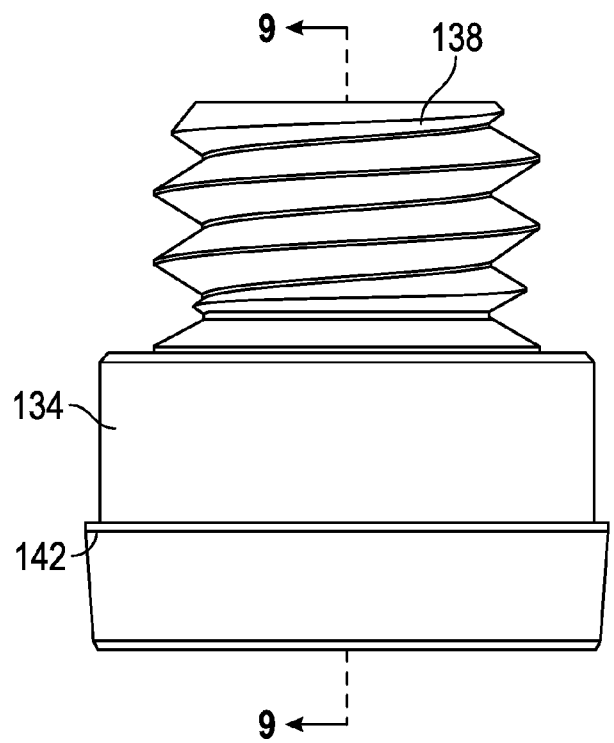
FIG. 8 is a side view illustration of the retention cap, according to an embodiment of the invention.
Figure 9:
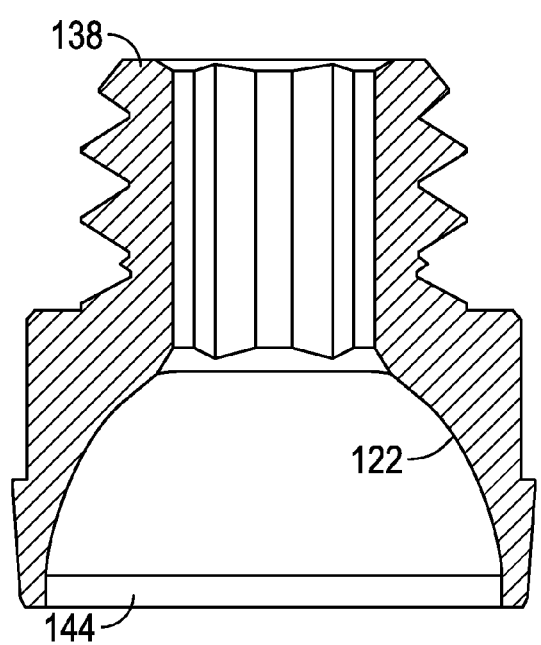
FIG. 9 is a side cutout view illustration of the retention member along lines 9-9 of FIG. 8 illustrating an inner spherical retention surface of the retention member, according to an embodiment of the invention.

FIGS. 7A-7D are illustrations of the retention cap 134 of the outer surface retention configuration, according to an embodiment of the invention, showing the threaded surface 138. FIG. 8 is a side view illustration of the retention cap 134 showing an acrylic finishing line 142 where acrylic from the surrounding denture can create a smooth finish with the denture cap, according to an embodiment of the invention; and FIG. 9 is a side cutout view illustration along lines 9-9 of FIG. 8 illustrating an inner spherical retention surface 122 of the retention cap 134, according to an embodiment of the invention. FIG. 9 also illustrates a retention cap 134 with a vertical surface 144 which serves as a wraparound retentive feature.

FIGS. 10A and 10B are side view and side cutout view illustrations, respectively, of an acrylic pick up cap 146 embodiment of the denture cap 136, according to an embodiment of the invention; and FIGS. 11A and 11B are side view and side cutout view illustrations, respectively, of a burn out cap 148 embodiment of the denture cap, according to an embodiment of the invention. The acrylic pick up cap 146 includes a plurality of retaining channels 150 that acrylic will flow through to hold a dental appliance such as a denture with the cap 146. The burn out cap 148 is used in cast bar situations.

FIGS. 12A and 12B are side view and side cutout view illustrations, respectively, of the abutment of the outer surface retention configuration, according to an embodiment of the invention. The abutment has an internal thread 152 for securing threaded components such as a healing collar, impression coping screw and Cantilever screw. Additionally, an internal driving feature 154 is visible, which serves to tighten the abutment into the implant.

Figure 13A:
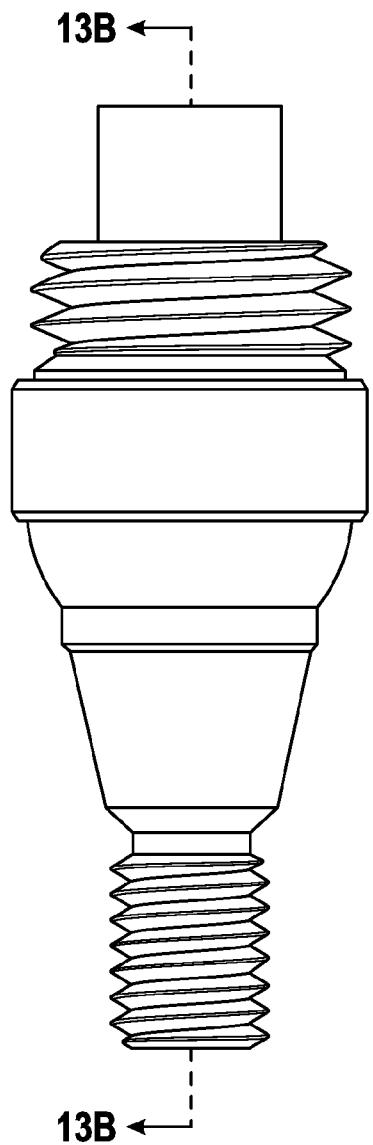
FIG. 13A is a side view of a screw-retained embodiment of the outer surface retention configuration, according to an embodiment of the invention.
Figure 13B:
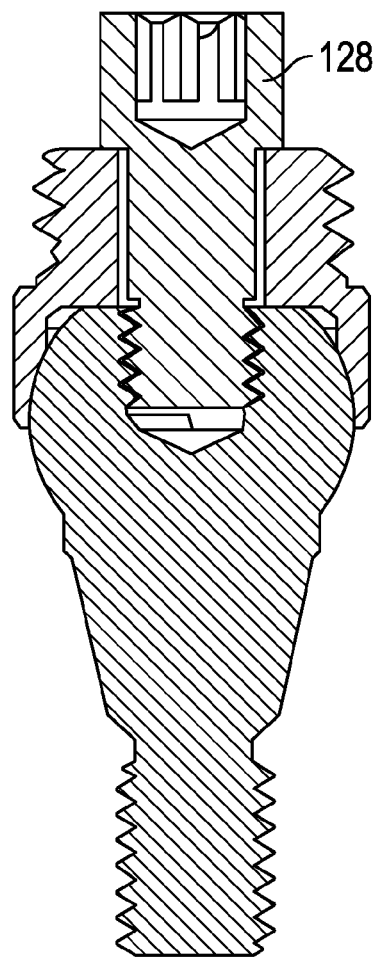
FIG. 13B is a side cutout view on the lines 13B-13B of FIG. 13A.
Figure 14A:
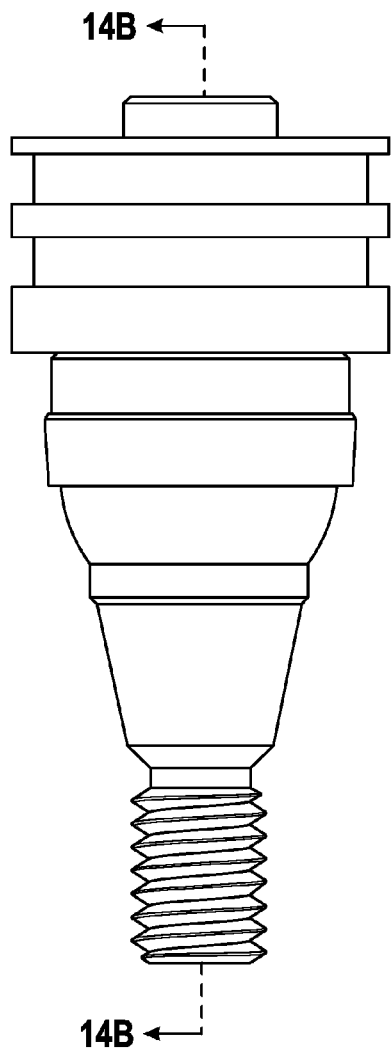
FIG. 14A is a side view of an acrylic pick up assembly of the screw-retained embodiment of the outer surface retention configuration, according to an embodiment of the invention.
Figure 14B:
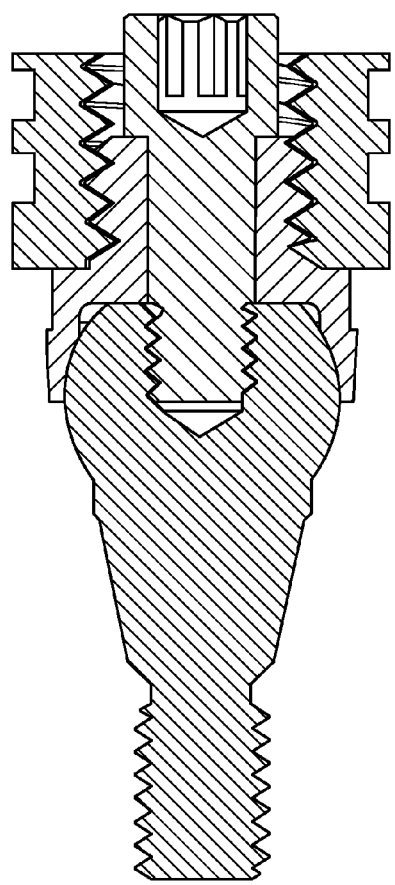
FIG. 14B is a side cutout view on the lines 14B-14B of FIG. 14A.
Figure 15A:
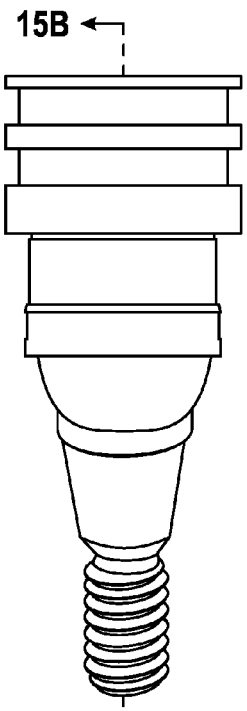
FIG. 15A is a side view of the acrylic pick up assembly of the outer surface retention configuration in an angled orientation, according to an embodiment of the invention.
Figure 15B:
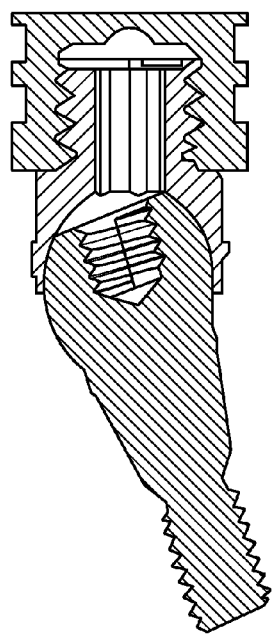
FIG. 15B is a side cutout view on the lines 15B-15B of FIG. 15A.
Figure 16A:
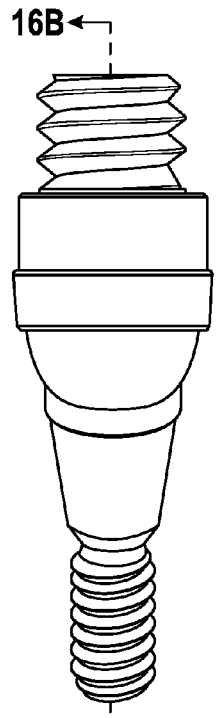
FIG. 16A is a side view of the outer surface retention configuration in an angled configuration, according to an embodiment of the invention.
Figure 16B:
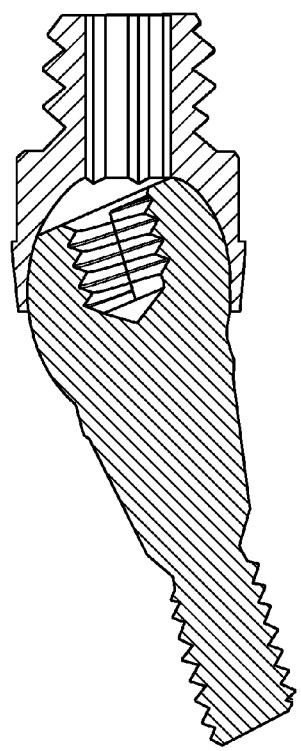
FIG. 16B is a side cutout view on the lines 16B-16B of FIG. 16A.

FIGS. 13A and 13B are side view and side cutout view illustrations, respectively, of a screw-retained embodiment of the outer surface retention configuration, according to an embodiment of the invention, where a cantilever screw 128 is secured through an opening of the retention cap 134 and into a threaded connection with the abutment 132. FIGS. 14A and 14B are side view and side cutout view illustrations, respectively, of an acrylic pick up assembly of the screw-retained embodiment of the outer surface retention configuration, according to an embodiment of the invention. FIGS. 15A and 15B are side view and side cutout view illustrations, respectively, of the acrylic pick up assembly of the outer surface retention configuration in an angled orientation, according to an embodiment of the invention. FIGS. 16A and 16B are side view and side cutout view illustrations, respectively, of the outer surface retention configuration in an angled orientation, according to an embodiment of the invention.

D. Method of Use

Figure 17:
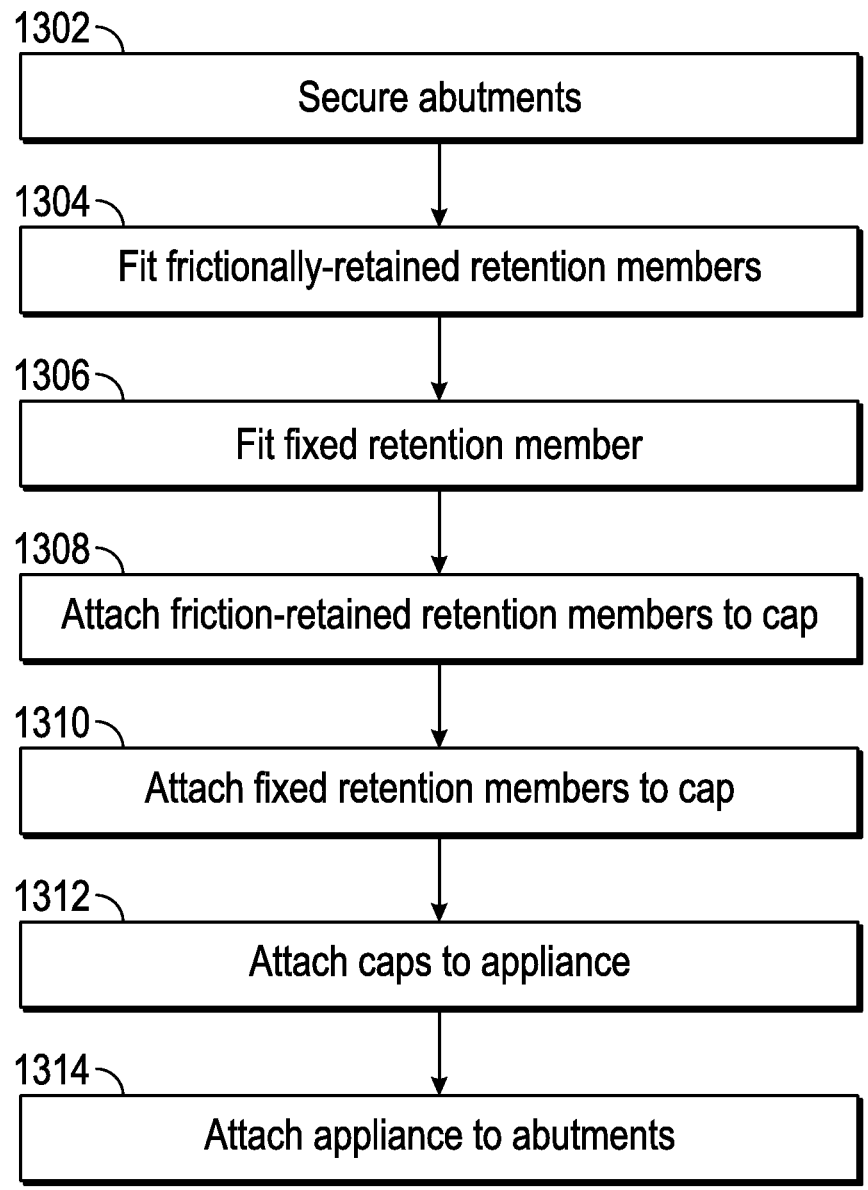
FIG. 17 is a flow diagram of a method of attaching a dental appliance with at least one dental attachment assembly, according to an embodiment of the invention.

FIG. 17 illustrates one embodiment of a method of attaching a dental appliance to a plurality of implants using the various dental attachment assemblies described herein. For example, where a patient is being fitted with a complete upper or lower denture, a plurality of implants will be inserted into the bone structure across the area where the denture is to be placed. In some embodiments, as few as 2 or as many as 6 implants may be used. In the embodiments described herein, the frictionally-retained dental attachment assembly may be utilized for the majority of the implants while fewer of the implants—even just one—will utilize the fixed, or screw-retained, dental attachment assembly. This provides flexibility in attaching the majority of the implants with the dental appliance while still providing a fixed connection at one implant which will ensure the retention of the entire dental appliance against any amount of retentive force.

In a first step 1302, an abutment is secured to an implant or other root structure that will support the dental appliance. Next, the frictionally-retained retention members are fitted onto at least one abutment (step 1304), and at least one fixed retention member is attached to at least one abutment (step 1306). In step 1308, the friction-retained retention members are attached to their respective caps, and in step 1310, the fixed retention members are attached to their respective caps. In step 1312 the non-swiveling retention member is removed from the cap and a swiveling retention member is inserted into the cap. In step 1312, the dental appliance may be engaged onto the abutment by the snap engagement of the retention member onto the abutment and may be swiveled or rotated into place through use of the swivel joint between the cap and retention member, which is further enhanced by the concave recess within the cap.

E. Dental Removal Tool and Pen

In one embodiment, a removal tool may be used to enable easy removal of the friction-retained dental appliance. The removal tool may comprise two parts—a removal loop and a removal pen. The removal loop may be a thin, circular loop partially inserted into a gap between a patient's gums and the dental appliance to create half loops on either side of the gap (i.e., an outer surface of the appliance and an inner surface of the appliance), and the removal pen may be a long, cylindrical shaft which is inserted into respective half loops present on either side of the gums when the circular loop is partially inserted. The removal pen is then used as a lever to pull or push against a portion of the dental appliance to separate the dental appliance from the gums.

Figure 18A:
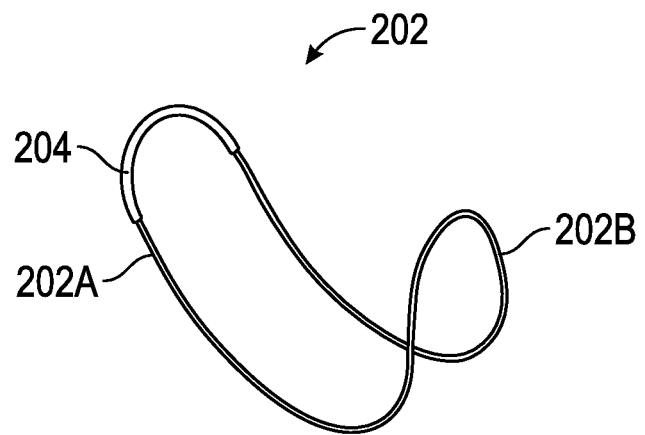
FIG. 18A illustrates one embodiment of a removal tool for removing the dental attachment assembly in a folded configuration, according to one embodiment of the invention.
Figure 18B:
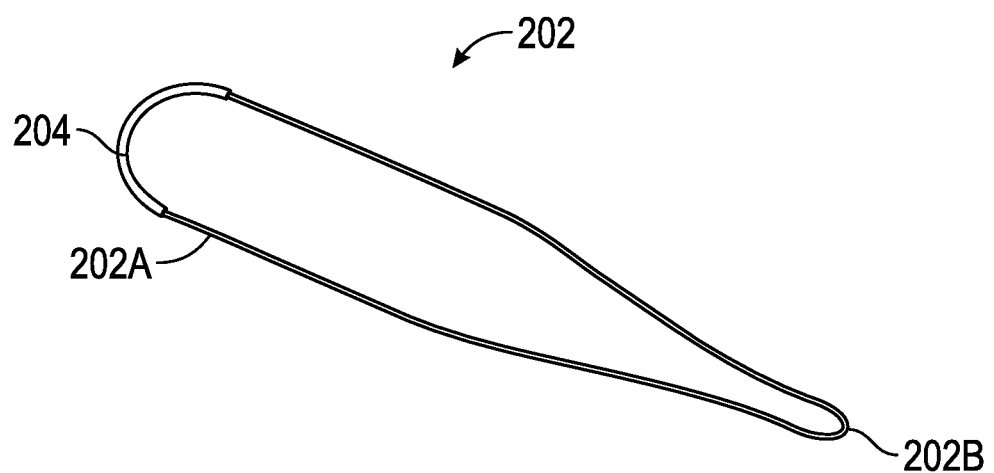
FIG. 18B illustrates one embodiment of the removal tool in an open configuration, according to one embodiment of the invention.

FIG. 18A and FIG. 18B illustrate one embodiment of the removal loop 202, which is the thin, circular loop that can be threaded between a gap between a patient's gum and the dental appliance, as will be shown below. The loop 202 may include a friction covering or larger diameter portion 204 on a first end 202A of the loop 202 where the removal pen 206 (shown below in FIG. 19B) will contact the loop 202 to minimize movement of the loop along the length of the removal pen 206. FIG. 18A illustrates the removal loop 202 in a folded configuration as it would appear once partially inserted into the gap between the gums and the dental appliance, while FIG. 18B illustrates the loop 202 in a flat, unfolded configuration prior to being inserted into the gap. As seen in FIG. 18B, the removal loop may also have a narrower diameter second end 202B to make it easier to insert into the gap.

Figure 19A:
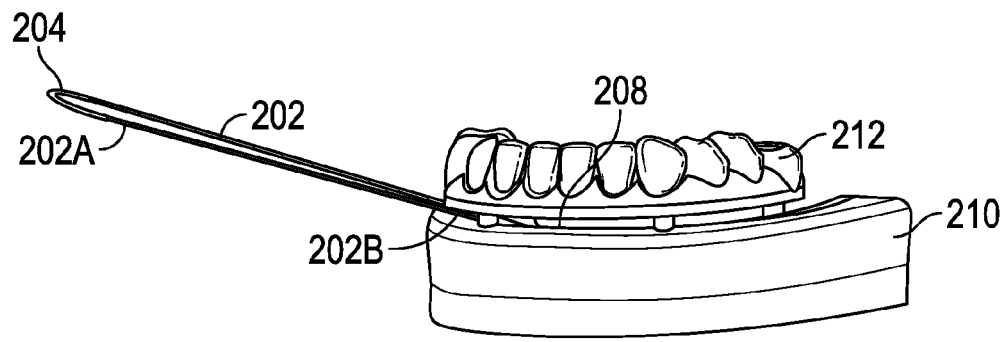
FIG. 19A and FIG. 19B are front perspective views and top views, respectively, of the removal tool partially inserted into a space between a patient's gums and an implant-retained denture, according to one embodiment of the invention.
Figure 19B:
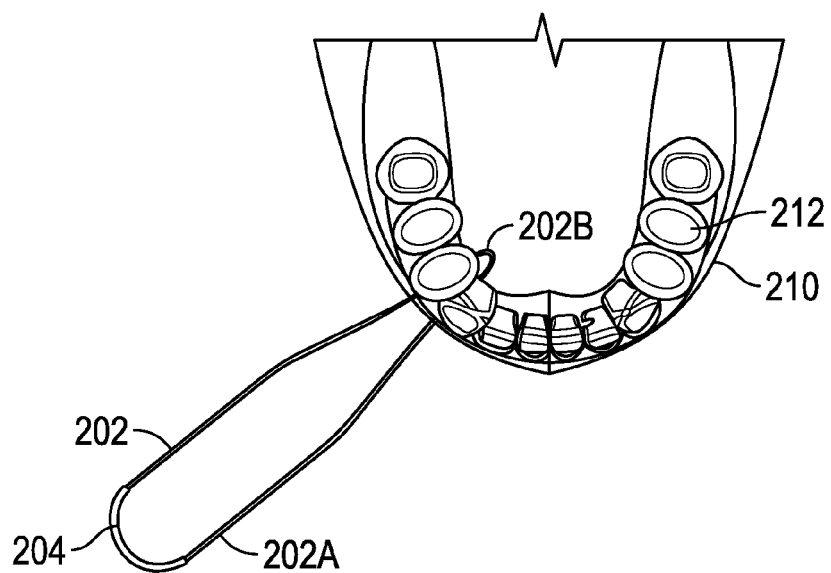
Figure 20A:
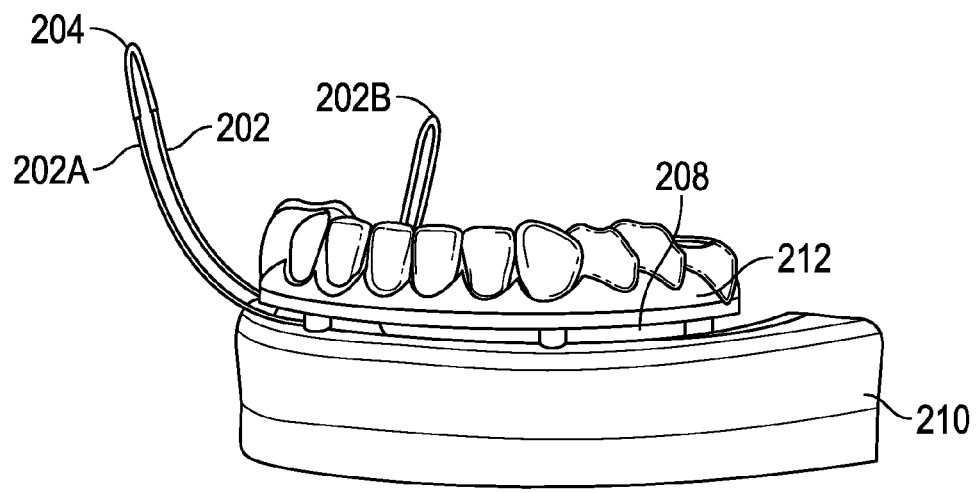
FIG. 20A is a side perspective view of the removal tool fully inserted into the space between the patient's gums and the implant-retained denture, according to one embodiment.
Figure 20B:
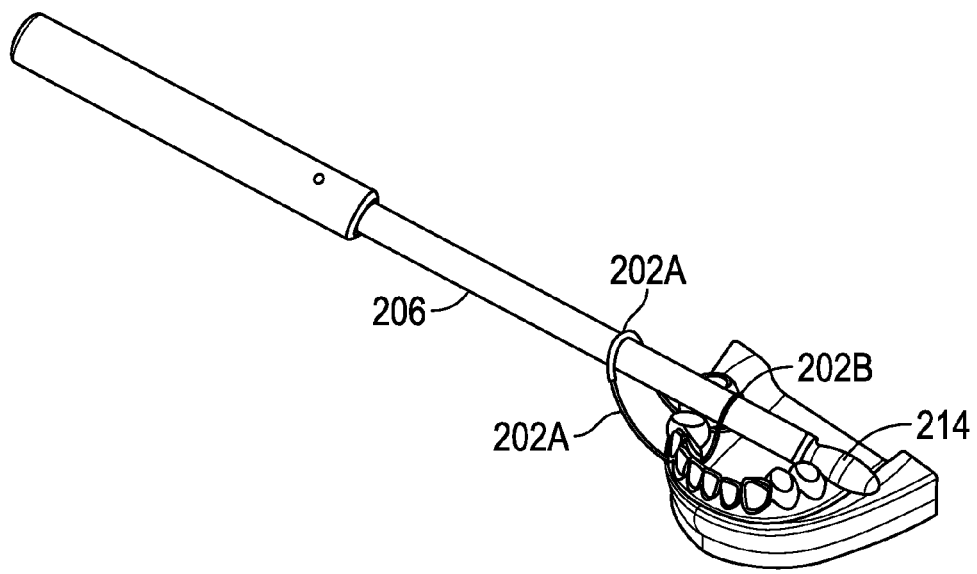
FIG. 20B is a top perspective view of the removal tool fully inserted into the space between the patient's gums and the implant-retained denture and being threaded by a removal pen, according to one embodiment.

FIG. 19A is a side perspective view illustration of the second end 202B of the removal loop 202 being inserted into a gap 208 between a patient's gums 210 and a dental appliance 212, according to one embodiment of the invention. FIG. 19B is a top perspective view illustration showing the narrow diameter second end 202B as it is initially threaded through the gap and exposed on an inner portion of the mouth and the dental appliance. In FIG. 20A, the loop 202 is partially inserted into the gap such that half of the loop where the first end 202A is located is visible on an outer portion of the mouth, while the half of the loop 202 where the second end 202B is located is visible on an inner portion of the mouth. When the loop 202 is moved into the folded configuration, as shown in FIG. 20A, the removal pen 206, shown in FIG. 20B, can be inserted through the half loop on the outer portion and the half loop on the inner portion of the mouth. In one embodiment, the removal pen 206 also includes a flexible end piece 214 which is designed to contact a top surface of the dental appliance where the user will apply pressure when removing the dental appliance 212 with the removal pen 206. With both half loops engaged, a user can then pull upwards (or downwards, depending on whether the appliance is on a bottom portion of the mouth or a top portion of the mouth) and use the force applied by the flexible end piece 214 on the dental appliance as a lever to lift the loop 202 away from the gap 208, thus using lever action to easily remove the dental appliance 212 without having to pull aggressively on the dental appliance or cause discomfort to the patient.

Figure 21A:
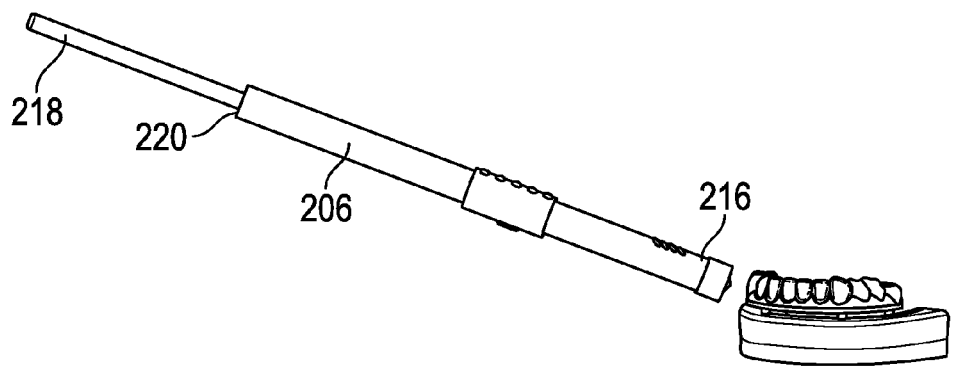
FIG. 21A is a side perspective view of a removal pen with an integrated retractable removal tool positioned adjacent to an implant-retained denture prior to initiating a process to remove the implant-retained denture, according to one embodiment.
Figure 21B:
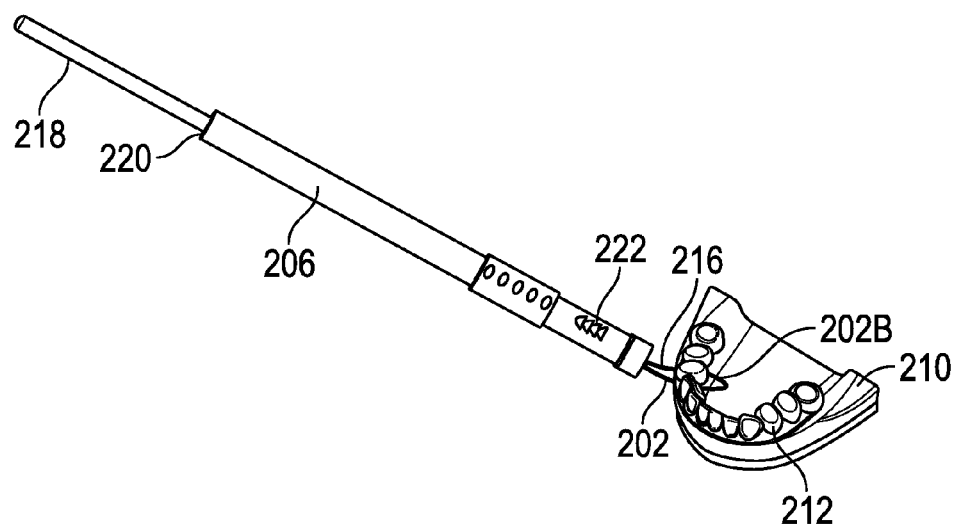
FIG. 21B is a top perspective view of the removal pen with the integrated retractable removal tool extending therefrom and being inserted into the space between the patient's gums and the implant-retained denture, according to one embodiment.
Figure 22A:
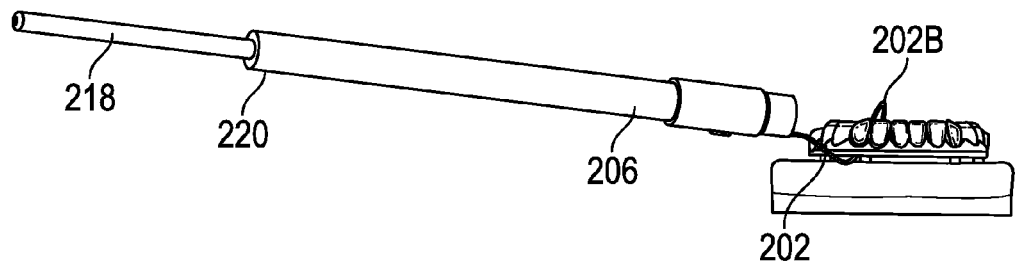
FIG. 22A is a side perspective view of the removal pen with the integrated retractable removal tool extending therefrom and inserted into the space between the patient's gums and the implant-retained denture embodiments of a removal tool and pen for removing the dental attachment assembly, according to one embodiment.
Figure 22B:
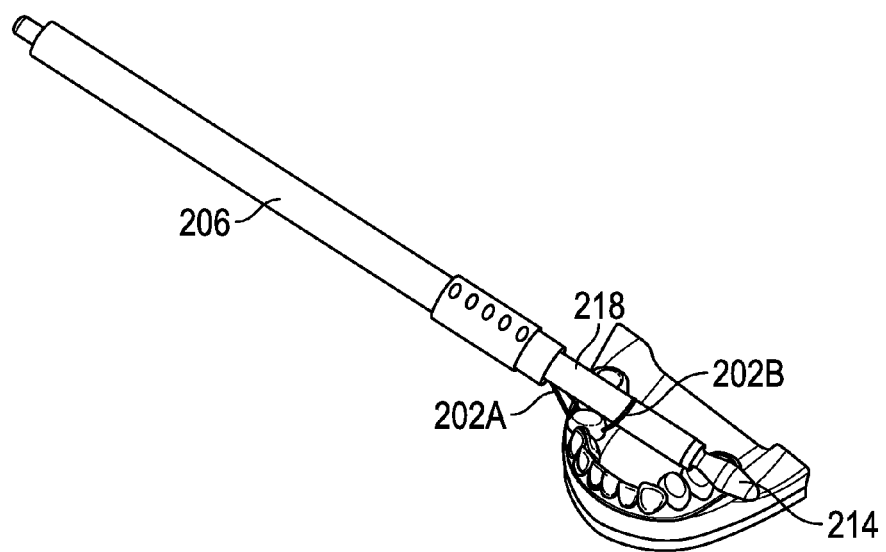
FIG. 22B is a top perspective view of a retractable extension rod which extends outwardly from the removal pen to provide leverage during removal of the dental attachment assembly, according to one embodiment of the invention.

An alternative embodiment of the removal tool 200 is illustrated in FIG. 21A, where the loop 202 is integrated into a proximal end 216 of the removal pen 206, and where the removal pen 206 is a housing which covers an extendible arm 218 which can extend from either the proximal end 216 or distal end 220 of the removal pen 206 to effectuate the removal operation. In operation, as shown in FIG. 21B, the loop 202 is extended from the proximal end 216 and into the gap between the gums and the dental appliance, as has been previously shown. The loop 202 may be extended from the pen 206 using a slider bar 222 or other advancing mechanism on the housing of the pen 206. Once the second 202B of the loop 202 is partially inserted into the gap, as shown in FIG. 22A, the user can then actuate the extendible arm 218 from an extended position on the distal end 220 to extend through the interior half loop and across the top surface of the dental appliance, as shown in FIG. 22B. Note that because the loop 202 is integrated into the pen 206, it does not need to extend through a half loop on the outer portion of the mouth since it is already connected with the loop on the outer portion. With the extendible arm 218 and the flexible end piece 214 now in position over the dental appliance, the same lever arm motion can be applied at the distal end of the pen 206 to effectuate the removal of the dental appliance from the dental attachment assembly.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A dental attachment assembly, comprising:
   a cap for securing with a dental appliance, the cap defining an inner cavity having an open end, an annular peripheral wall and an inner end wall;
   an abutment configured with an outer opening and a socket extending inward from the outer opening, the socket having an annular inward projection spaced from the outer opening; and
   a set of compressible retention members each comprising a shaft having a first end configured for attachment to the inner end wall of the cavity in the cap, and an enlarged head at a second end of the shaft which is at least partially spherical and has a maximum diameter greater than a diameter of the annular inward projection, the head being frictionally detachably attachable with the annular inward projection of the abutment socket to provide a predetermined level of retention force; and
   the set of compressible retention members having heads configured to provide different amounts of retention force;
   wherein the enlarged head of at least one compressible retention member has a series of spaced flattened portions extending around a maximum diameter portion of the head for providing a reduced retention force.

2. The dental attachment assembly of claim 1, wherein the inner end wall of the cavity in the cap has a threaded bore; and
   the shaft of each compressible retention member has a threaded portion configured for threaded engagement with the threaded bore in the cap.

3. The dental attachment assembly of claim 1, wherein the compressible retention member and abutment are securely retained at an angle of approximately 20 degrees.

4. The dental attachment assembly of claim 1, wherein the shaft of each compressible retention member is flexible.

5. The dental attachment assembly of claim 1, wherein the set of compressible retention members comprise at least a first retention member having a head with a first diameter and a second retention member having a head with a second diameter larger than the first diameter, the second retention member providing a higher retention force than the first retention member.

* * * * *